United States Patent [19]

Murao et al.

[11] Patent Number: 5,354,685
[45] Date of Patent: Oct. 11, 1994

[54] SUIDATRESTIN AND PRODUCTION THEREOF

[75] Inventors: Sawao Murao, Sakai; Takashi Shin, Sanda; Kyoichi Sugawa, Hirakata; Amachi Teruo, Takarazuka, all of Japan

[73] Assignee: S. Murao, Sakai, Japan

[21] Appl. No.: 40,184

[22] Filed: Mar. 29, 1993

[30] Foreign Application Priority Data

Mar. 31, 1992 [JP] Japan .................. 4-077627

[51] Int. Cl.$^5$ .................. C12N 1/20; C12N 9/98; C12P 1/06
[52] U.S. Cl. .................. 435/253.5; 435/712; 435/169; 435/183; 435/187; 435/252.1; 435/886; 424/115
[58] Field of Search ............ 435/169, 183, 187, 252.1, 435/253.5, 886, 71.2; 424/115

[56] References Cited

U.S. PATENT DOCUMENTS

| | | | |
|---|---|---|---|
| 4,010,258 | 3/1977 | Murao | 424/115 |
| 4,526,866 | 7/1985 | Kido et al. | 435/169 |
| 4,565,781 | 1/1986 | Otake et al. | 435/85 |
| 4,686,185 | 8/1987 | Wakunaga | 435/253.5 |
| 4,757,001 | 7/1988 | Ashihara et al. | 435/184 |
| 4,759,928 | 7/1988 | Gurusiddaiah et al. | 435/169 |
| 4,923,990 | 5/1990 | Nakano et al. | 546/84 |
| 4,954,641 | 9/1990 | Sato et al. | 549/384 |
| 5,091,524 | 2/1992 | Vertesy et al. | 435/169 |
| 5,164,507 | 11/1992 | Sasaki et al. | 546/310 |
| 5,169,778 | 12/1992 | Murao et al. | 435/254 |

FOREIGN PATENT DOCUMENTS 55-68292A 5/1980 Japan .
WO90/10010 7/1990 PCT Int'l Appl. .

OTHER PUBLICATIONS

Aps Abs Japan 04–99792 Nakajima et al Pub Abs Jul. 22, 1992.
Aps Abs Japan 58–210025 Nakano Pub. Date Abs Mar. 9, 1984 "Antitrehalase Antibody".
Aps Abs Japan 55–68294 Ooya et al Pub Date Jul. 30, 1980 "Production of Trehalase Inhibitor S–GI Using Microorganism".

*Primary Examiner*—Herbert J. Lilling
*Attorney, Agent, or Firm*—David G. Conlin; George W. Neuner

[57] ABSTRACT

A novel trehalase inhibitor having the following physicochemical properties:
(1) Activity: a specific inhibitory activity to trehalase;
(2) Form: white powder, water-soluble;
(3) Somogy-Nelson test: negative
(4) Rydon-Smith test: positive
(5) Optical rotation $[\alpha]_D^{23}$: 113.8° (C, 0.1 $H_2O$)
(6) Molecular weight: 335 ($[M+H]^+ = 336$)
(7) Ultraviolet absorption spectrum: 258.5 nm (max.)
(8) $^{13}C$-NMR(ppm): 28.9, 41.0, 56.9, 58.4, 64.3, 65.0, 71.3, 74.0, 75.2, 75.8, 76.0, 77.1, 123.0, 144.7

2 Claims, No Drawings

SUIDATRESTIN AND PRODUCTION THEREOF

FIELD OF THE INVENTION

The invention relates to a novel trehalase inhibitor. The invention further relates to an actinomycete capable to producing Suidatrestin and to a method for the production of Suidatrestin by using the actinomycete.

PRIOR ART

Trehalase is an enzyme which decomposes trehalose into its unit monosaccharide, glucose. It is known that said enzyme is present not only in small intestine and kidney of mammals but also in fungi and insects in which trehalose is a main source of energy for living activity. Trehalase is therefore an important enzyme which plays a main part in energy-metabolism in fungi and insects. In contrast, there is observed no useful role of the enzyme in kidney and small intestine of mammals. Recently, Validmaycin which specifically inhibit the trehalase of *Rhizoctonia solani* bacter was found, and it has used as an antifungal agent. Furthermore we found the inhibitor, Trehalostatin, which has a specific effect to the trehalases of insects and we also have been studied its use as an antifungal agent and insectcide. However, it is anticipated that there will be an appearance of fungi and insects which are resistant to the above agents. Accordingly, it has been desired to develop a new trehalase inhibitor which has a difference structure and inhibitory characteristics from the prior trehalase inhibitors.

SUMMARY OF THE INVENTION

It was considered that a trehalase inhibitor which specifically inhibit the mammalian trehalases might inhibit a trehalases having resistance to the conventional trehalase inhibitors. Additionally, because trehalases have not an important role in mammals, it can be expected that the trehalase inhibitor has a minimum side effect to mammals.

Accordingly, the present inventors had searched widely in nature for a microorganism which can produce a substance capable of strongly inhibiting a trehalase in porcine small intestine. The present inventors had found that actinomycete belonged to a genus of Streptomyces, which had isolated from soil, produced a new substance which showed an inhibitory effect to trehalase of animals especially mammalian small intestine with a very low concentration, in both their culture medium and mycobiont. The new substance had been named as "Suidatrestin". The actinomycete according to the present invention is preferably a strain SAM 1953 isolated from soil.

The SAM 1953 strain has the following bacteriological properties:

(1) Morphological characteristics

The substrate and aerial mycelium was 0.4–0.5 μm in width and well diverged. The substrate mycelium was branched. Fragmentation of the substrate mycelium was not observed. The aerial mycelium is also branched and formed spore chains with more than 10 spores per chain. The spore chains formed loops, hooks, and sometimes imperfect spirals. The spores were spherical to cylindrical in shape and 0.8 to 1.0 μm in diameter. The spore surface was smooth. No sporangia, synnemate, or selerotia were observed even after 14 days cultivation.

(2) Cultural characteristics (28° C., 14 days culture)

Sucrose.nitrate agar medium; growth: poor; aerial hypha: slight, light brown; reverse side of colony: light brown; soluble pigment: none Glucose.asparagine agar medium; growth: good; aerial hypha: abundant, yellow; reverse side of colony: dark orange; soluble pigment: none Glycerine.asparagine agar medium; growth: good; aerial hypha: abundant; ashy brown; reverse side of colony: ashy brown; soluble pigment: none Starch.inorganic salt agar medium; growth: good; aerial hypha: abundant, dark green; reverse side of colony: ashy brown; soluble pigment: none Tyrosine agar medium; growth: good; aerial hypha: abundant, brownish ash; reverse side of colony: reddish brown; soluble pigment: none Nutrient agar medium; growth: good; aerial hypha: abundant, white; reverse side of colony: white; soluble pigment: none Yeast-extraction.malt-extraction agar medium; growth: good, aerial hypha: abundant, greeny ash; reverse side of colony: dark brown; soluble pigment: yellowish brown Oat meal agar medium; growth: good, aerial hypha: abundant, brownish ash; reverse side of colony: yellow; pigment: none Tap water agar medium; growth: poor, aerial hypha: poor, reverse side of colony: semitransparency; soluble pigment: none 1/10 carrot.potato agar medium; growth: good; aerial hypha: abundant, brown; reverse side of colony: brown; soluble pigment: none 1/10V-8juice agar medium; growth: good; aerial hypha: abundant, ashy brown; reverse side of colony: brown; soluble pigment: none (3) Physiological characteristics 1) Growth temperature As a result of culture tests conducted at temperature of 12.5° C., 15.5° C., 18.0° C., 21.0° C., 23.5° C., 26.0° C., 28.5° C., 30.5° C., 33.0° C., 35.5° C., 38.5° C. and 41.0° C. by using a trypton.yeast extract liquid medium, the temperature range for growth was 12.5° to 41.0° C., with optimum growth occuring 21.0°–38.5° C.

| 2) Liquefaction of gelatin | |
|---|---|
| glucose.peptone.gelatin medium | positive |
| simple gelatin medium | positive |
| meat extract.gelatin medium | positive |
| 3) Hydrolysis of starch | positive |
| 4) Coagulation of skim milk (28° C.) | negative |
| 5) Peptonization of skim milk | positive |
| 6) Formation of melanoid pigment | |
| peptone.yeast-extract iron agar medium | negative |
| tyrosine agar medium | negative |
| tryptone yeast-extract agar medium | negative |
| 7) Reduction of nitrate | negative |

8) Utilization of Carbohydrates of carbon source (determined in the basal medium of Pridham and Gottlieb (ISP-9) at 28° C. for 14 days)

| | |
|---|---|
| D-glucose | + |
| D-xylose | + |
| L-rhamnose | − |
| L-arabinose | + |
| D-fructose | + |
| Raffinose | − |
| D-mannitol | + |
| Inositol | − |
| Sucrose | − |

| | |
|---|---|
| Lactose | + |
| Salicin | ± |

(+; utilized, ±; doubtful to use, −; not utilized)

(4) Chemotaxonomy 1) 2,6-diaminopimelic acid

By investigations of the whole body of the strain according to the method of Staneck, J. L. and Roberts, G. D. method (Applied Microbiology Vol. 28, P. 226, 1974), there was observed LL-2,6-diaminopimelic acid.

2) Menaquinones

The principal menaquinone component is MK-9 (Hb, H8).

According to those taxonomic properties, the SAM 1953 strain was identified as an actinomycete belonging to the genus Streptmyces. Thus, this present invention can use any strain that belongs to the genus Streptomyces and provides Suidatrestin. The strain SAM 1953 was named as Streptomyces sp. SAM 1953, and was deposited with Fermentation Research Institute Agency of Industrial Science and Technology, Ministry of International Trade and Industry 1-3, Higashi 1-chome, Tsukuba-shi, Ibaraki-ken, 305, Japan, on Mar. 25, 1992 (Accession No FERM BP-3805).

In present invention, the above actinomycete may be cultured with either liquid or solid medium. However, it is usually advantageous to carry out a shaking culture with the liquid medium or aeration-agitation culture. Any medium may be used, in which the actinomycete according to the present invention can grow and the product of the present invention can be accumulated. Namely, there may be used as carbon source glucose, lactose, starch, sucrose, dextrin, molasses, organic acids etc. and there may be used as nitrogen source protein hydrolysate such as peptone casamino acid, and also meat-extact, yeast-extract, soybean cake, corn steep liquor, amino acid, ammonium salt, nitrate, and other organic or inorganic nitrogen compounds.

Further, it may be added as an inorganic salt many types of phosphate, magnesium sulfate, sodium chloride, and the like, as well as vitamins, compound bearing nucleic acid -associated compounds in order to promote the growth of the strain. Sometimes, it is effective to add an antifoaming agent such as silicon, polypropylene-glycol derivatives and soybean oil into the medium for increseing an amount of accumulation of the novel substance according to the present invention.

It is preferable to carry out a small-scale preculture and to inoculate the culture product into a main culture medium. In both the main culture and preculture, the culture conditions such as temperature, period, medium properties may be selected and regulated so as to obtain a maximum amount of accumulation of the novel substance of this invention, but it is usually preferable to maintain the culture under aerobic condition at a temperature of from 25° C. to 40° C. The pH value of a liquid medium is preferably kept in a range of from 5.5 and 8.0.

When the liquid medium is used for culture, a desired product is mainly accumulated in a liquid part. It is therefore desired to remove cells by filtration or centrifugation and separate them from supernatant of filtrate. It is also possible, if desired, to obtain the desired product directly from the culture medium.

The inhibitory activity of Suidatrestin in each step during purification is determined by the following method.

Inhibitor solution (50 μl) and trehalase solution (porcine entrails) 50 μl are mixed, and incubated at 37° C. for 5 min. After addition of 400 μl of 5 mM phosphate buffer (pH 6.3) containing 5 mM trehalose, the resulting mixture is incubated at 37° C. for 15 min. and stopped by adding 1N hydrochloric acid (30 μl). Then, into these 100 ul reactant solution, there are added 0.1M phosphate buffer (pH6.5) 2.5 ml, 4 mM ABTS 25 μl, 3.5-diaminobenzoic acid 25 μl, and horseradish-peroxidase aqueous solution (1 mg/ml) 10 μl. The resulting mixture is incubated at 37° C. for 5 min., then mixed with glucose-oxidase solution (1 mg/ml) 100 μl and further incubated at 37° C. for 10 min., followed by addition of 1M sodium azide aqueous solution (100 μl) to measure absorbance at 550 nm and obtain an amount of a produced glucose.

In this method, a concentration of Suidatrestin which inhibits activity of the enzyme(trehalase) by 50% is estimated as one unit/ml.

The present substance may be separated and purified by various methods based on the chemical characteristics of the same product.

The Suidatrestin may be isolated as a white and amorphous powder by, for example, treatment with an organic solvent, gel-filtration with cephadex and biogel, ion-exchange chromatography with various in o-exchange resins adsorption chromatography with adsorbent such as Amberlite-XAD-1 and XAD-2, active carbon, silicagel, normal-phase chromatography with a carrier such as YMC-PA43 and TSK-Amide 80, or optional combination thereof. Other methods may be used so long as the properties of the present substance are effectively utilized.

An especially preferred combination of the adsorbents are that of Dawex 50W-X2(H+), active carbon, YMC-PA43 and TSK-Amide 80.

The novel substance thus obtained has properties shown in the following examples. It shows the inhibitory activity to trehalase of fungi, insects, especially of porcine small intestine under a very low concentration as shown in the examples. It is therefore very useful as fungicide, insecticide, or anti-corpulency diabetes agent.

Further, the present substance can be used not only in an isolated form but also as the culture product per se of Suidatrestin-producing or simply purified one therefrom.

The present invention will be explained in detail with reference to the following examples which should not be construed as limiting the scope of the invention.

EXAMPLE

Example 1

Production of Suidatrestin

Pure culture of SAM 1953 strain 60 ml was inoculated in the medium (pH 7.0, 6 l) containing glucose, yeast-extract, peptone, and magnesium sulfate, and subjected to aeration-agitation culture for 120 hrs in three 10 l jar-fermenters (33° C. 200 rpm, 1 vvm). Cells were removed from these culture fluid by filtration using filterpaper (TOYO-ROSHI, No.2). The resulting filtrate was passed through a column (Dowex 50W-X2 (H+) 3.5 l), equilibrated with deionized water so as to adsorb a portion of trehalase-inhibiting activity.

The column was washed with deionized water of 6-column volume and the portion of trehalase-inhibiting activity was eluted with 0.1N NH4OH of 16-column volume. The eluate was fractioned by 500 ml to collect fractions of trehalase-inhibiting activity.

Ammonia was removed from the fractions of trehalase-inhibiting activity by using an evaporator to a final volume of 300 ml. A part of the resulting concentrate was loaded onto CK08P (Na+) column (2.5 $\phi \times 20$ cm) equilibrated with 20 mM sodium phosphate buffer so as to adsorb trehalase-inhibiting activity. The column was washed with 500 ml of the same buffer and trehalase-inhibiting activity was eluted out with a linear-gradient consisting of 500 ml each of 20 mM sodium phosphate buffer (pH 6.0) and 0.2M sodium phosphate buffer (pH 8.8). The same operations were repeated on the other concentrates.

The trehalase-inhibiting activity fractions thus obtained were adsorbed to an active carbon column (2.5 $\phi \times 10$ cm) washed with sufficient water. The column was washed with 700 ml of deionized water and the trehalase-inhibiting activity portion was eluted with 500 ml of 30% MeOH.

The trehalase-inhibiting activity fractions thus obtained were concentrated to 5 ml by an evaporator and the concentrate was subjected to re-chromatography with CK08P(Na+) column (2.5 $\phi \times 20$ cm). The fractions of trehalase-inhibiting activity thus obtained were concentrated to 5 ml by using an evaporator, injected into a Carbonex column washed with distilled water, washed with distilled water, and eluted with 0–30% MeOH gradient.

The fractions of trehalase-inhibiting activity thus obtained were concentrated to 2 ml by using an evaporator, injected into YMC PA43 column equilibrated with acetonitrile:distilled water=75:25(v/v) and developed with the same solvent.

The fractions of trehalase-inhibiting activity thus obtained were concentrated to 2 ml by using an evaporator, injected into TSK-Amide 80 column (1.0 $\phi \times 45$ cm) equibrated with acetonitrile:distilled water=65:35 (v/v) containing 20 mM sodium phosphate beffer (pH 5) and developed with the same solvent to monitor the absorbance of eluate on 210 nm. In this chromatography, trehalase-inhibiting activity was eluted as a single peak showing absorbance on 210 nm.

The fractions of trehalase-inhibiting activity thus obtained were concentrated to 2 ml by using an evaporator and subjected to re-chromatography with Carbonex column.

The fractions of trehalase-inhibiting activity thus obtained were concentrated to 2 ml by using an evaporator, injected into Asahipak NH2P-50 column equilibrated with acetonitrile:distilled water=85:15 (v/v), and developed with the same solvent. By concentrating, drying and lyophilizing trehalase-inhibiting activity fractions with diluted HCl, the desired product was obtained in a pure form (1 mg).

Example 2

Physicochemical Properties of Suidatresin

The substance obtained from the culture of SAM 1953 strain according to Example 1 was named Suidatrestin.

Physicochemical properties were illustrated below.
Form: white powder; water-soluble
Somogy-Nelson test: negative
Rydon-Smith test: positive
Optical rotation $[\alpha]_D^{23}$: 113.8° (C, 0.1, H$_2$O)
Molecular weight: 335 ([M+H]+ =336)
Ultraviolet absorption spectrum: 258.5 nm (max.)
$^{13}$C-NMR(ppm): 28.9, 41.0, 56.9, 58.4, 64.3, 65.0, 71.3, 74.0, 75.2, 75.8, 76.0, 77.1, 123.0, 144.7

Example 3

The Enzyme Inhibiting Spectrum of Suidatrestin

The trehalase-inhibiting activity of Suidatrestin was measured against various trehalases.

| Origin of trehalase | ID$_{50}$ (ng) |
|---|---|
| porcine small intestine | 0.21 |
| Aldrichina grahami | 1.05 |
| fungi | 0.93 |

What is claimed is:

1. Isolated Streptomyces sp. SAM 1953, having the identifying characteristics of FERM BP-3805.

2. An isolated and biologically pure culture of Streptomyces sp. SAM 1953, having the identifying characteristics of FERM BP-3805, which shows an inhibitory effect against trehalase in animals.

* * * * *